US011504336B2

(12) United States Patent
Saxena et al.

(10) Patent No.: US 11,504,336 B2
(45) Date of Patent: Nov. 22, 2022

(54) EXTENDED RELEASE PHARMACEUTICAL COMPOSITION OF CLOZAPINE

(71) Applicant: INTAS PHARMACEUTICALS LTD., Ahmedabad (IN)

(72) Inventors: Mayank Saxena, Sanand (IN); Rikin Patel, Sanand (IN); Piyush Kansagra, Sanand (IN); Balvir Singh, Sanand (IN); Ashish Sehgal, Sanand (IN)

(73) Assignee: INTAS PHARMACEUTICALS LTD., Gujarat (IN)

( * ) Notice: Subject to any disclaimer, the term of this patent is extended or adjusted under 35 U.S.C. 154(b) by 155 days.

(21) Appl. No.: 16/334,115

(22) PCT Filed: Sep. 16, 2017

(86) PCT No.: PCT/IB2017/055615
§ 371 (c)(1),
(2) Date: Mar. 18, 2019

(87) PCT Pub. No.: WO2018/051292
PCT Pub. Date: Mar. 22, 2018

(65) Prior Publication Data
US 2020/0054573 A1 Feb. 20, 2020

(30) Foreign Application Priority Data
Sep. 17, 2016 (IN) .............................. 201621031726

(51) Int. Cl.
| A61K 9/50 | (2006.01) |
| A61K 9/20 | (2006.01) |
| A61K 9/51 | (2006.01) |
| A61K 31/5513 | (2006.01) |
| A61K 9/00 | (2006.01) |
| A61K 9/48 | (2006.01) |
| A61K 47/10 | (2017.01) |
| A61K 47/12 | (2006.01) |
| A61K 47/38 | (2006.01) |

(52) U.S. Cl.
CPC .......... *A61K 9/5073* (2013.01); *A61K 9/2077* (2013.01); *A61K 9/5015* (2013.01); *A61K 9/5047* (2013.01); *A61K 9/5192* (2013.01); *A61K 31/5513* (2013.01)

(58) Field of Classification Search
CPC .. A61K 31/5513; A61K 9/5073; A61K 47/10; A61K 47/12; A61K 47/38; A61K 9/0053; A61K 9/2077; A61K 9/4866; A61K 9/5015; A61K 9/5047; A61K 9/5089; A61K 9/5192
See application file for complete search history.

(56) References Cited

U.S. PATENT DOCUMENTS

| 3,539,573 A | 11/1970 | Schmutz |
| 2008/0026040 A1 | 1/2008 | Farr et al. |
| 2008/0026062 A1 | 1/2008 | Farr et al. |
| 2010/0260858 A1 | 10/2010 | Ruddy et al. |
| 2011/0300210 A1 | 12/2011 | Swanson et al. |
| 2015/0283092 A1 * | 10/2015 | Ruddy ................. A61K 31/436 424/495 |

FOREIGN PATENT DOCUMENTS

| IN | 2001MU00465 A | 5/2001 |
| WO | 2006/059194 A2 | 6/2006 |
| WO | 2006059194 A2 | 6/2006 |
| WO | 2007036671 A2 | 4/2007 |
| WO | 2007/056424 A2 | 5/2007 |
| WO | 2007056424 A2 | 5/2007 |
| WO | 2010118232 A1 | 10/2010 |

OTHER PUBLICATIONS

International Search Report PCT/IB2017/055615, prepard by the Indian Patent Office dated of completion Mar. 1, 2018, 2 pages.
Agnihotri, Formulation and evaluation of novel tableted chitosan microparticles for the controlled release of clozapine, Journal of Microencapsulation, Nov. 2004, vol. 21, No. 7, pp. 709-718.
(Shanmugam S. Granulation techniques and technologies: recent progresses. Bioimpacts. 2015;5(1):55-63).

* cited by examiner

*Primary Examiner* — Jeffrey T. Palenik
(74) *Attorney, Agent, or Firm* — Brooks Kushman P.C.

(57) ABSTRACT

An extended release pharmaceutical composition of Clozapine The extended release composition of Clozapine provides an extended release pharmaceutical composition having Clozapine, a seal coating, an acidic coating, and an extended release coating. The composition is particularly suitable for dispensing a once-a-day solid oral pharmaceutical formulation which releases a therapeutically effective amount of Clozapine over an extended time period.

1 Claim, No Drawings

EXTENDED RELEASE PHARMACEUTICAL COMPOSITION OF CLOZAPINE

CROSS-REFERENCE TO RELATED APPLICATION

This application is the U.S. national phase of PCT Application No. PCT/IB2017/055615 filed on Sep. 16, 2017, which is related to Indian Provisional Application No. IN201621031726 filed on Sep. 17, 2016, the disclosures of which are incorporated in their entirety by reference herein.

FIELD OF THE INVENTION

This present invention relates to an extended release pharmaceutical composition of Clozapine or its pharmaceutically acceptable salts thereof and process for preparation of the same.

BACKGROUND OF THE INVENTION

Clozapine is classified as an "atypical" antipsychotic drug. The chemical name for Clozapine is 8-chloro-11-(4-methyl-1-piperazinyl)-5H-dibenzo[b,e][1,4]diazepine with the following structure formula:

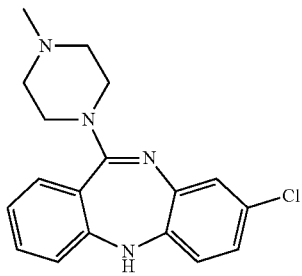

FIG. 1: Clozapine

Clozapine is a yellow, crystalline powder, very slightly soluble in water. The molecular formula is $C_{18}H_{19}ClN_4$ and the molecular weight of 326.83.

Clozapine is used for the management of severely ill schizophrenic patients who fail to respond adequately to standard drug treatment for schizophrenia. Clozapine is also used for reducing the risk of recurrent suicidal behavior in patients with schizophrenia or schizoaffective disorder who are judged to be at chronic risk for reexperiencing suicidal behavior, based on history and recent clinical state. Clozapine is also used in the treatment of parkinson related psychosis. Suicidal behavior refers to actions by a patient that put him/herself at risk for death.

Clozapine was first disclosed in the U.S. Pat. No. 3,539,573 and is classified as an atypical antipsychotic agent. Clozapine is marketed by Novartis in the US as CLOZARIL® tablets.

Clozapine shows a wide inter-individual variation in plasma half-life with mean value of 6±1.5 hours. Even though Clozapine is well absorbed from GIT, it undergoes extensive first pass metabolism and only 27-50% of the dose reaches systemic circulation unchanged. Hence, extended release formulation is necessary. Moreover, the use of extended release products offers potential advantages like sustained blood levels, attenuation of adverse effects and improved patient compliance. Particularly, in case of psychosis, patient is unable to take medication frequently; hence, the development of extended release formulations is necessary for patient compliance. Thus, formulating Clozapine in an extended release form will increase the therapeutic efficacy and patient compliance.

In prior art, many techniques have been used to provide sustained and extended-release pharmaceutical compositions of Clozapine in order to maintain therapeutic levels of medicaments and to minimize the effects of missed doses of drugs caused by a lack of patient compliance. Some of sustained release compositions for Clozapine described in prior art are as follows:

US20110300210 discloses a controlled release nanoparticulate formulations of Clozapine and a rate-controlling polymer which prolong the release of the Clozapine for a time period ranging from about 2 to about 24 hours or longer.

WO2010118232 discloses a composition has a semipermeable coating; particles of Clozapine having an effective average particle size of less than or about 2 µm and a surface stabilizer adsorbed on the surface of the Clozapine particles; and a solubilizing agent.

US20080026062 discloses a composition of plurality of nano-sized particles of active agent and water-soluble or partially water-soluble polymer matrix wherein particulate pharmaceutical composition is micronized.

US20080026040 discloses plurality of polymeric film layers heat sealed together as a multilayer structure; and controlled amounts of active agent dissolved or dispersed in a liquid vehicle and method of preparation of this by ink-jetting.

EP1931320 discloses microparticles "shell" coated with at least one active ingredient and is of the kind formed by particles of active pharmaceutical each covered by at least two distinct coating film IN2001MUM00465 discloses matrix technology for the preparation of pharmaceutical composition for controlled release of Clozapine.

Clozapine is BCS Class II drug substance having pH dependent solubility. Clozapine is soluble in acidic pH and practically insoluble in basic pH. As Clozapine is insoluble in intestinal pH, extended release formulation releasing drug substance in later part of GI tract have minimal contribution to in vivo therapeutic effect. Thus it is very difficult to develop the extended release formulation of Clozapine.

All above reference mentions about either multi layer structure or matrix base technology. The inventors of the present invention have developed an extended release Clozapine formulation.

OBJECTS OF THE INVENTION

The object of the present invention is to provide an extended release pharmaceutical composition of Clozapine or its pharmaceutically acceptable salts.

Another object of the present invention to provide an extended release pharmaceutical composition of Clozapine in the form of multiparticulates like granules, pellets, beads, spheroids or the likes thereof.

Another object of the present invention to provide an extended release pharmaceutical formulation of Clozapine, wherein the said pharmaceutical composition in the form of multiparticulates are dispensed or compressed in the form of tablets or mini-tablets or filled in capsules.

Another object of the present invention is to provide an extended release pharmaceutical composition of Clozapine in the form of multiparticulates like granules, pellets, beads, spheroids or the likes thereof comprising:

a) Granules, pellets, beads or spheroids comprising Clozapine,
b) Optional seal coating with hydrophilic polymer,
c) Acidic coating with acidic substance, and
d) Extended release coating with a water insoluble polymer and a water soluble polymer.

Another object of the present invention is to provide an extended release pharmaceutical composition of Clozapine in the form of multiparticulates like granules, pellets, beads, spheroids or the likes thereof comprising:
a) Granules, pellets, beads or spheroids comprising Clozapine,
b) Acidic coating with acidic substance, and
c) Extended release coating with a water insoluble polymer and a water soluble polymer.

Another object of the present invention is to provide an extended release pharmaceutical composition of Clozapine in the form of multiparticulates like granules, pellets, beads, spheroids or the likes thereof comprising:
a) Granules, pellets, beads or spheroids comprising Clozapine,
b) Seal coating comprising hydrophilic polymer,
c) Acidic coating comprising acidic substance, and
d) Extended release coating comprising a water insoluble polymer and a water soluble polymer.

Another object of the present invention is to provide an extended release pharmaceutical composition of Clozapine in the form of multiparticulates like granules, pellets, beads, spheroids or the likes thereof comprising:
a) Granules, pellets, beads or spheroids comprising Clozapine,
b) Seal coating comprising hydrophilic polymer,
c) Acidic coating comprising acidic substance, and
d) Extended release coating comprising a water insoluble polymer and a water soluble polymer.

Another object of the present invention is to provide an extended release pharmaceutical composition of Clozapine in the form of multiparticulates like granules, pellets, beads, spheroids or the likes thereof comprising:
a) Granules, pellets, beads or spheroids comprising Clozapine,
b) Seal coating comprising hydrophilic polymer,
c) Acidic coating comprising acidic substance and osmotic agent, and
d) Extended release coating comprising a water insoluble polymer and a water soluble polymer.

Another object of the present invention is to provide a capsule of Clozapine comprising:
a) Granules, pellets, beads or spheroids comprising Clozapine,
b) seal coating comprising hydrophilic polymer,
c) Acidic coating comprising acidic substance and osmotic agent, and
d) Extended release coating comprising a water insoluble polymer and a water soluble polymer.

Another object of the present invention is to provide a capsule of Clozapine comprising:
a) Clozapine,
b) seal coating comprising hydrophilic polymer on the Clozapine,
c) Acidic coating comprising acidic substance and osmotic agent on the seal coat, and
d) Extended release coating comprising a water insoluble polymer and a water soluble polymer.

Another object of the present invention is to provide an extended release pharmaceutical composition of Clozapine in the form of multiparticulates like granules, pellets, beads, spheroids or the likes thereof comprising:
a) Granules, pellets, beads or spheroids comprising Clozapine,
b) seal coating comprising hydrophilic polymer,
c) Acidic coating comprising acidic substance and osmotic agent, and d) Extended release coating comprising a water insoluble polymer and a water soluble polymer;
wherein the ratio of acidic substance to Clozapine is 0.5:1 to 1:1 weight by weight (W/W).

Another object of the present invention to provide a process for the preparation of an extended release pharmaceutical composition of Clozapine in the form of multiparticulates like granules, pellets, beads, spheroids or the likes thereof.

Another object of the present invention is to provide an extended release pharmaceutical composition of Clozapine comprises acidic coating, wherein the said acidic coating comprises an acidic substance and one or more pharmaceutically acceptable excipient(s).

Another object of the present invention is to provide an extended release pharmaceutical composition of Clozapine comprises osmotic agent.

Another object of the present invention is to provide an extended release pharmaceutical composition of Clozapine comprises acidic coating, wherein the said acidic coating comprises an acidic substance and an osmotic agent.

Another object of the present invention is to provide an extended release pharmaceutical composition of Clozapine comprises seal coating, wherein the said seal coating comprises hydrophilic polymer.

Another object of the present invention is to provide an extended release pharmaceutical composition of Clozapine comprises extended release coating, wherein the said extended release coating comprises water insoluble polymer and a water soluble polymer.

Another object of the present invention is to provide an extended release pharmaceutical composition of Clozapine comprises extended release coating, wherein the extended release coating comprising a water insoluble polymer and a water soluble polymer wherein the water soluble polymer can act as pore former and/or a plasticizer.

Another object of the present invention is to provide an extended release pharmaceutical composition of Clozapine release a therapeutically effective amount of the Clozapine over an extended time period.

Another object of the present invention is to provide an extended release pharmaceutical composition of Clozapine, wherein release of Clozapine from the composition is extended up to 24 hours.

Another object of the present invention is to provide an extended release pharmaceutical composition of Clozapine, wherein the said composition is filled in capsules to provide pharmaceutical formulation of Clozapine for oral administration.

Another object of the present invention is to provide an extended release pharmaceutical composition of Clozapine, wherein the said composition is dispensed or compressed in the form of tablets or mini-tablets or filled in capsules to provide pharmaceutical formulation of Clozapine for oral administration.

Another object of the present invention is to provide an extended release pharmaceutical composition of Clozapine, wherein the said composition is filled in capsules to provide pharmaceutical formulation of Clozapine for oral administration.

Another object of the present invention is to provide process for preparation of an extended release pharmaceutical composition of Clozapine as exemplified herein

SUMMARY OF THE INVENTION

The present invention relates to an extended release pharmaceutical composition of Clozapine. The present invention provide an extended release pharmaceutical composition comprising Clozapine, a seal coating, an acidic coating, and an extended release coating. The invention is particularly suitable for dispensing a once-a-day solid oral pharmaceutical formulation which releases a therapeutically effective amount of Clozapine over an extended time period.

DETAILED DESCRIPTION

Unless otherwise indicated, terms in this specification are intended to have their ordinary meaning in the relevant art.

The inventors of the present invention have surprisingly found that it is possible to develop a stable and extended release pharmaceutical composition of Clozapine which is dispensed as a once-a-day solid oral pharmaceutical formulation, which releases a therapeutically effective amount of Clozapine over an extended time period.

Thus, the object of the present invention is to provide an extended release pharmaceutical composition of Clozapine.

Further, the present invention is to provide an extended release pharmaceutical composition of Clozapine in the form of multiparticulates like granules, pellets, beads, spheroids or likes thereof.

The term "extended release" as used herein before and throughout the description refers to drug delivery system releasing a clozapine at a predetermined rate, locally or systemically, for a specified period of time. Extended release can be used interchangeably with prolonged release, programmed release, timed release, sustained release, controlled release, and modified release, slow release and other such dosage forms.

The term "Clozapine" used throughout the specification refers to not only clozapine per se, but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof. It is also possible to use any salts and free base form of clozapine.

The term "pharmaceutical composition" means multiparticulates in the form of granules, pellets, beads, spheroids or likes thereof. The said pharmaceutical composition according to the present invention, is dispensed or compressed in the form of tablets or mini-tablets or filled in capsules to provide pharmaceutical formulation of Clozapine for oral administration.

The term "pharmaceutical formulation" means suitable dosage form for oral administration in the form of tablet, mini tablets or capsules.

The term "multiparticulates" means a plurality of granules, pellets, beads, spheroids or likes thereof, irrespective of their size, shape or morphology.

The term "seal coat" is synonymous to various terms like separating layer, seal coating layer, intermediate layer, barrier coating layer, film coating and the like. The Seal coat comprises the substances but not limited to water-soluble substance, water-insoluble substance and one or more pharmaceutically acceptable excipient(s). Specifically the seal coat comprises hydrophilic polymer.

Suitable "seal coating" agent is selected from hydrophilic polymer, hydroxypropyl methylcellulose, specifically lower viscosity grade of hydroxypropyl methylcellulose and like thereof.

The term "extended release coat" mainly comprises of extended release polymers and optionally other pharmaceutically acceptable excipients; wherein the extended release coat extends the release of clozapine. Specifically the extended release coat comprises a water insoluble polymer and a water soluble polymer wherein the water soluble polymer act as pore former and/or a plasticizer.

Suitable "water soluble polymer" may include but not limited to polyethylene glycol, PEG 400 and like thereof.

Suitable "plasticizer" may include but not limited to glycerin, polyethylene glycol, PEG 400, polyethylene glycol monomethyl ether, propylene glycol, sorbitol sorbitan solution or mixtures and like thereof.

The term "acidic coat" mainly comprises of acidic substance, which helps in providing an acidic pH micro-environment between the upper part of the small intestine and the lower part of the large intestine. The acidic pH micro-environment improves solubility and bioavailability of Clozapine.

In yet another embodiment of the present invention is to provide an extended release pharmaceutical composition of Clozapine in the form of multiparticulates like granules, pellets, beads, spheroids or the likes thereof comprising:
a) Granules, pellets, beads or spheroids comprising Clozapine,
b) Optional seal coating with hydrophilic polymer,
c) Acidic coating with acidic substance, and
d) Extended release coating with a water insoluble polymer and a water soluble polymer.

In yet another embodiment of the present invention is to provide an extended release pharmaceutical composition of Clozapine in the form of multiparticulates like granules, pellets, beads, spheroids or the likes thereof comprising:
a) a plurality of cores, wherein the cores consists of granules, pellets, beads or spheroids comprising Clozapine and at least one diluent,
b) Acidic coating with acidic substance, and
c) Extended release coating with a water insoluble polymer and a water soluble polymer.

In yet another embodiment of the present invention is to provide an extended release pharmaceutical composition of Clozapine in the form of multiparticulates like granules, pellets, beads, spheroids or the likes thereof comprising:
a) Granules, pellets, beads or spheroids comprising Clozapine,
b) Seal coating comprising hydrophilic polymer,
c) Acidic coating comprising acidic substance, and
d) Extended release coating comprising a water insoluble polymer and a water soluble polymer.

In yet another embodiment of the present invention is to provide an extended release pharmaceutical composition of Clozapine in the form of multiparticulates like granules, pellets, beads, spheroids or the likes thereof comprising:
a) Granules, pellets, beads or spheroids comprising Clozapine,
b) Seal coating comprising hydrophilic polymer,
c) Acidic coating comprising acidic substance, and
d) Extended release coating comprising a water insoluble polymer and a water soluble polymer.

In yet another embodiment of the present invention is to provide an extended release pharmaceutical composition of Clozapine in the form of multiparticulates like granules, pellets, beads, spheroids or the likes thereof comprising:

a) Granules, pellets, beads or spheroids comprising Clozapine,
b) Seal coating comprising hydrophilic polymer,
c) Acidic coating comprising acidic substance and osmotic agent, and
d) Extended release coating comprising a water insoluble polymer and a water soluble polymer.

In yet another embodiment of the present invention is to provide a capsule of Clozapine comprising:
a) Granules, pellets, beads or spheroids comprising Clozapine,
b) Seal coating comprising hydrophilic polymer,
c) Acidic coating comprising acidic substance and osmotic agent, and
d) Extended release coating comprising a water insoluble polymer and a water soluble polymer.

In yet another embodiment of the present invention is to provide a capsule of Clozapine comprising beads which comprises:
a) Clozapine,
b) Seal coating comprising hydrophilic polymer on the Clozapine,
c) Acidic coating comprising acidic substance and osmotic agent on the seal coat, and
d) Extended release coating comprising a water insoluble polymer and a water soluble polymer.

In yet another embodiment of the present invention is to provide an extended release pharmaceutical composition of Clozapine in the form of multiparticulates like granules, pellets, beads, spheroids or the likes thereof comprising:
a) Granules, pellets, beads or spheroids comprising Clozapine,
b) Seal coating comprising hydrophilic polymer,
c) Acidic coating comprising acidic substance and osmotic agent, and
d) Extended release coating comprising a water insoluble polymer and a water soluble polymer.

wherein the ratio of acidic substance to Clozapine is 0.5:1 to 1:1 by weight by weight (W/W).

In yet another embodiment of the present invention is to provide a process for the preparation of extended release pharmaceutical composition of Clozapine in the form of multiparticulates like granules, pellets, beads, spheroids or the likes thereof.

In another embodiment of the present invention to provide an extended release pharmaceutical composition of Clozapine comprises acidic coating.

In yet another embodiment of the present invention to provide an extended release pharmaceutical composition of Clozapine comprises acidic coating, wherein the said acidic coating comprises an acidic substance, osmotic agent and optionally one or more pharmaceutically acceptable excipient(s).

Suitable "acidic substance" may include but not limited to tartaric acid, citric acid, fumaric acid, adipic acid or mixtures and like thereof.

Yet another embodiment of the present invention is to provide an extended release pharmaceutical composition of Clozapine comprising an osmotic agent.

Suitable "osmotic agent" may include but not limited to polyethylene glycol, sucrose, glucose, fructose, sodium chloride, magnesium chloride, potassium nitrate or mixtures and like thereof.

Yet another embodiment of the present invention is to provide an extended release pharmaceutical composition of Clozapine comprises seal coating, wherein the said seal coating comprises hydrophilic polymer.

Yet another embodiment of the present invention is to provide an extended release pharmaceutical composition of Clozapine comprises extended release coating, wherein the said extended release coating comprises water insoluble polymer and a water soluble polymer.

In yet another embodiment of the present invention is to provide an extended release pharmaceutical composition of Clozapine comprising acidic coating and extended release coating with optional seal coating.

Suitable "polymers" may include water soluble and water insoluble polymers. Suitable polymers may include one or more of cellulosic polymers/copolymers or its derivatives including methyl cellulose, hydroxypropyl methylcellulose, hydroxyethyl cellulose, hydroxypropyl cellulose, hydroxyethyl methylcellulose, carboxymethylcellulose, sodium carboxymethylcellulose; polyethylene oxides, chitosan, gums, starch derivatives, polyurethanes, polysaccharides, polyalcohols, cellulose derivatives as ethyl cellulose, ethyl cellulose aqueous dispersion, cellulose acetate, poly (alkyl) methacrylate, copolymers of acrylic or methacrylic acid esters, eudragit, polymethacrylates containing quaternary ammonium group, high molecular weight polyvinyl alcohols, polyvinyl acetate dispersion (eg: Kollidon), waxes, hydrogenated vegetable oil, fatty acids; long chain fatty alcohols, cellulose acetate butyrate or mixtures thereof and other materials known to one of ordinary skill in the art.

Preferably, the water insoluble polymer used in extended release coating is cellulose derivatives such as ethyl cellulose and like thereof.

Pharmaceutically acceptable excipient(s) include but are not limited to binders, fillers or diluents, lubricants, osmotic agent, plasticizer, glidants or solvent(s) and mixtures thereof. One excipient can perform more than one function. All excipients can be used at levels well known to the persons skilled in the art may be selected from but are not limited to starches such as potato starch, wheat starch, corn starch; microcrystalline cellulose; celluloses such as hydroxypropyl cellulose, hydroxyethyl cellulose, hydroxypropylmethyl cellulose, ethyl cellulose, sodium carboxy methyl cellulose; polyethylene oxide, polyvinyl pyrrolidone, poly-N-vinyl amide, polyethylene glycol, gelatin, poly propylene glycol, carbohydrates, confectioner's sugar, compressible sugar, dextrates, dextrin, dextrose, fructose, lactitol, mannitol, sucrose, lactose, calcium phosphate dibasic or tribasic, calcium sulphate, Mg, Al or Ca or Zn stearate, glyceryl behenate, mineral oil, sodium stearyl fumarate, stearic acid, talc, silicon dioxide, magnesium trisilicate, powdered cellulose, talc, tribasic calcium phosphate, calcium silicate, magnesium silicate, colloidal silicon dioxide, croscarmellose sodium, povidone, guar gum, magnesium aluminium silicate, sodium alginate, sodium starch glycolate and other materials known to one of ordinary skill in the art and combinations thereof.

Solvents may be used in present invention include all the solvents well known in the art or their mixtures thereof are selected from the group comprising methyl alcohol, ethyl alcohol, isopropanol, methylene chloride, acetone, acetonitrile, purified water, or mixture thereof.

In yet another embodiment of the present invention provide an extended release pharmaceutical composition of Clozapine release a therapeutically effective amount of the Clozapine over an extended time period.

In yet another embodiment the present invention provide an extended release pharmaceutical composition of Clozapine, wherein release of Clozapine from the composition is extended up to 24 hours.

Yet another embodiment the present invention is to provide an extended release pharmaceutical composition of Clozapine, wherein the said composition is filled in capsules to provide pharmaceutical formulation of Clozapine for oral administration.

The composition of the invention is suitable for schizophrenia, reducing the risk of recurrent suicidal behavior in patients with schizophrenia or schizoaffective disorder, parkinson related psychosis, suicidal behavior refers to actions by a patient that put him/herself at risk for death.

EXAMPLES

The following examples are illustrative of the present invention, and the examples should not be considered as limiting the scope of this invention in any way, as these examples and other equivalents thereof will become apparent to those versed in the art, in the light of the present disclosure.

Example 1

| Sr. no. | Ingredients | Mg/cap |
|---|---|---|
| 1 | Clozapine | 12.5-300 |
| 2 | Microcrystalline Cellulose | 6-215 |
| 3 | PEG 4000 | 2-55 |
| 4 | Hydroxypropyl Cellulose | 0.2-9 |
| 5 | Hypromellose | 1-30 |
| 6 | Tartaric Acid | 7-190 |
| 7 | Sodium Chloride | 3-75 |
| 8 | Ethyl Cellulose | 3-100 |
| 9 | PEG 400 | 0.3-40 |
| 10 | Talc | 0.05-2 |

Manufacturing Process:
1. Sift Clozapine, microcrystalline cellulose, and hydroxypropyl cellulose through proper mesh
2. Prepare solution of PEG 4000 in purified water.
3. Granulate material obtained in step 1 using solution obtained in step 2 in rapid mixer granulator.
4. Prepare extrude of step-3 granules using extruder and the spheronize using spheronizer.
5. Dry the spheroids obtained in step 4 in fluid bed processor.
6. Prepare seal coating solution by dissolving hypropmellose E5 in purified water and seal coat the spheroids obtained in step 5 in fluid bed processor.
7. Dissolve tartaric acid and sodium chloride in purified water and spray on to the seal coated spheroids obtained step 6 in fluid bed processor.
8. Prepare solution of ethyl cellulose and PEG 400 in isopropanol and dichloromethane and spray on to the spheroids obtained in step-7 in fluid bed processor.
9. Blend the spheroids obtained in step 8 with talc in blender for 5 minute.
10. Fill spheroids of step 9 in to empty capsule shell size "00".

Example 2

| Sr. no. | Ingredients | % W/W |
|---|---|---|
| 1 | Clozapine | 30.9 |
| 2 | Microcrystalline Cellulose | 21.9 |
| 3 | PEG 4000 | 4.9 |
| 4 | Hydroxypropyl Cellulose | 0.9 |
| 5 | Hypromellose | 2.9 |
| 6 | Tartaric Acid | 19.3 |
| 7 | Sodium Chloride | 7.7 |
| 8 | Ethyl Cellulose | 10.1 |
| 9 | PEG 400 | 1.0 |
| 10 | Talc | 0.2 |

Example 3

| Sr. no. | Ingredients | % W/W |
|---|---|---|
| 1 | Clozapine | 30.9 |
| 2 | Microcrystalline Cellulose | 22.0 |
| 3 | PEG 4000 | 4.9 |
| 4 | Hydroxypropyl Cellulose | 0.9 |
| 5 | Hypromellose | 2.9 |
| 6 | Tartaric Acid | 19.3 |
| 7 | Sodium Chloride | 7.7 |
| 8 | Ethyl Cellulose | 10.0 |
| 9 | PEG 400 | 1.0 |
| 10 | Talc | 0.2 |

Manufacturing Process:
Example 2 and 3 was prepared according to the process given in example 1.

Example 4

| Sr. no. | Ingredients | % W/W |
|---|---|---|
| 1 | Clozapine | 32.6 |
| 2 | Microcrystalline Cellulose | 16.7 |
| 3 | PEG 4000 | 5.5 |
| 4 | Hydroxypropyl Cellulose | 0.6 |
| 5 | Hypromellose E5 | 2.8 |
| 6 | Tartaric Acid | 20.4 |
| 7 | Sodium Chloride | 8.2 |
| 8 | Ethyl Cellulose | 9.1 |
| 9 | PEG 400 | 3.9 |
| 10 | Talc | 0.2 |

Manufacturing Process:
1. Sift Clozapine, microcrystalline cellulose, and hydroxypropyl cellulose through suitable mesh
2. Prepare solution of PEG 4000 in purified water.
3. Granulate material obtained in step 1 using solution obtained in step 2 in rapid mixer granulator.
4. Prepare extrude of step-3 granules using extruder and the spheronize using spheronizer.
5. Dry the spheroids obtained in step 4 in fluid bed processor.
6. Prepare seal coating solution by dissolving hypropmellose E5 in purified water and seal coat the spheroids obtained in step 5 in fluid bed processor.
7. Dissolve tartaric acid and sodium chloride in purified water and coat on step-6 seal coated spheroids in fluid bed Processor.
8. Prepare extended release coating solution of Ethyl cellulose and PEG 400 in Isopropanol and dichloromethane. Coated pellets of step 7 to be coated with extended release coating solution using fluid bed processor.
9. Blend extended release coated spheroids of Step-8 with talc in blender for 5 min.
10. Fill spheroids of step 9 in to empty capsule shell size "00".

Example 5

| Sr. no. | Ingredients | % W/W |
|---|---|---|
| 1 | Clozapine | 32.9 |
| 2 | Microcrystalline Cellulose | 18.5 |
| 3 | PEG 4000 | 4.1 |
| 4 | Hydroxypropyl Cellulose | 0.8 |
| 5 | Hypromellose | 1.7 |
| 6 | Tartaric Acid | 20.6 |
| 7 | Sodium Chloride | 8.2 |
| 8 | Ethyl Cellulose | 11.9 |
| 9 | PEG 400 | 1.2 |
| | Total | 100 |

Example 6

| Sr. no. | Ingredients | % W/W |
|---|---|---|
| 1 | Clozapine | 28.4 |
| 2 | Microcrystalline Cellulose | 16.0 |
| 3 | Lactose | 7.1 |
| 4 | Hydroxypropyl Cellulose | 1.1 |
| 5 | Opadry II 85F18422 | 2.6 |
| 6 | Tartaric Acid | 17.7 |
| 7 | Sodium Chloride | 14.2 |
| 8 | Ethyl Cellulose | 11.9 |
| 9 | PEG 400 | 1.2 |
| | Total | 100 |

Manufacturing Process:

Example 5 and 6 was prepared according to the process similar to the process given in example 1.

Example 7: Effect of pH on Solubility of Clozapine

| Sr. no. | Ingredients | % W/W |
|---|---|---|
| 1 | Clozapine | 50.0 |
| 2 | Microcrystalline Cellulose | 20.0 |
| 3 | Lactose Monohydrate | 28.1 |
| 4 | Hydroxy propyl Cellulose | 1.9 |
| 5 | P. Water | q.s |

Manufacturing Process:

1. Sift Clozapine and microcrystalline cellulose, lactose monohydrate and hydroxy propyl Cellulose through suitable mesh
2. Transfer material of Step-1 in rapid mixer granulator and granulate using purified water.
3. Prepare extrude of step-2 granules using extruder and the spheronize using spheronizer.
4. Dry the step-3 spheroids in Fluid bed dryer.

The composition obtained in example 7 was evaluated for solubility and dissolution and dissolution profiles are tabulated below.

| Sr. no. | Product | Cumulative % average drug release (Time in min) | | | | | | |
|---|---|---|---|---|---|---|---|---|
| | | 0 | 15 | 30 | 45 | 60 | 90 | 120 |
| 1 | 0.1N HCl/Basket/100 RPM/900 ml | | | | | | | |
| | % Release | 0 | 96 | 101 | 102 | 102 | 102 | 102 |
| 2 | Phosphate buffer pH 6.0/Basket/100 RPM/900 ml | | | | | | | |
| | % Release | 0 | 6 | 10 | 14 | 18 | 24 | 28 |
| 3 | Phosphate buffer pH 6.8/Basket/100 RPM/900 ml | | | | | | | |
| | % Release | 0 | 3 | 4 | 7 | 9 | 10 | 13 |

From the above dissolution data that it can be concluded that Clozapine exhibit pH dependent solubility.

Example 8: Drug Loading with Tartaric Acid (i.e. without Seal Coating)

| Sr. no. | Ingredients | % W/W |
|---|---|---|
| 1 | Clozapine | 36.6 |
| 2 | Sugar Sphere (#30-35) | 18.3 |
| 3 | Tartaric Aid | 22.9 |
| 4 | Sodium Chloride | 9.2 |
| 5 | P. Water | q.s. |
| 6 | Ethyl Cellulose 10 Cps | 11.9 |
| 7 | PEG 400 | 1.2 |
| 8 | Suitable solvents | q.s. |
| 9 | EHG Capsules | 1 No |

Manufacturing Process:

1. Clozapine was dispersed in purified water.
2. Tartaric acid and sodium chloride was separately dissolved in purified water.
3. Solution of step-2 was added to step-1 under constant stirring and stirred till clear solution obtained.
4. Sugar sphere was loaded to fluid bed processor and coated with step-3 solution.
5. PEG 400 and ethyl cellulose were added to isopropyl alcohol and stirred will to disperse.
6. Dichloromethane was added to step-5 and stirred to get clear solution.
7. Drug coated pellets of step-4 were transferred to fluid bed processor and coated with step-6 solution.

Example 9

| | | % W/W | | | |
|---|---|---|---|---|---|
| Sr. no. | Ingredients | 9a | 9b | 9c | 9d |
| 1 | Clozapine USP | 30.9 | 32.6 | 32.6 | 32.4 |
| 2 | Microcrystalline Cellulose | 21.9 | 16.7 | 16.7 | 13.9 |
| 3 | PEG 4000 | 4.9 | 5.5 | 5.5 | 5.5 |
| 4 | Hydroxypropyl Cellulose | 0.9 | 0.6 | 0.6 | — |
| 5 | Hypromellose E5 | 2.9 | 2.8 | 2.8 | 2.6 |
| 6 | Tartaric Acid | 19.3 | 20.4 | 20.4 | 24.3 |
| 7 | Sodium Chloride | 7.7 | 8.2 | 8.2 | 8.1 |
| 8 | Ethyl Cellulose 10 cps | 10.1 | 9.8 | 9.1 | 9.1 |
| 9 | PEG 400 | 1.0 | 3.3 | 3.9 | 3.9 |
| 10 | Talc | 0.2 | 0.2 | 0.2 | 0.3 |
| | Total | 100 | 100 | 100 | 100 |

Manufacturing Process:

All four batches of example 9 were prepared by according to the process given in example 1.

Dissolution Profiles of Batches of Example 9:

| Sr. no. | Batch No | \multicolumn{10}{c}{Cumulative % drug dissolved at (Time in Hour)} |
|---|---|---|---|---|---|---|---|---|---|---|
|  |  | 0 | 1 | 2 | 4 | 8 | 10 | 12 | 16 | 20 | 24 |
| 1 |  | \multicolumn{10}{l}{pH 6.8 Phosphate buffer} |
|  | 9a | 0 | 2 | 20 | 50 | 75 | 81 | 85 | 91 | 94 | 95 |
| 2 |  | \multicolumn{10}{l}{pH 6.8 Phosphate buffer} |
|  | 9b | 0 | 14 | 37 | 63 | 77 | 81 | 83 | 84 | 88 | 88 |
| 3 |  | \multicolumn{10}{l}{pH 6.8 Phosphate buffer} |
|  | 9c | 0 | 27 | 56 | 76 | 87 | 89 | 90 | 92 | 92 | 92 |
| 4 |  | \multicolumn{10}{l}{pH 6.8 Phosphate buffer} |
|  | 9d | 0 | 30 | 57 | 78 | 89 | 93 | 95 | 97 | — | — |

From the above dissolution data that it can be concluded that extended release composition according to present invention gives extended release up to 24 hours.

Effect of Seal Coat on Stability:

Stability data of composition of example 8 (without seal coat) and of example 9a (with seal coat) were compared.

| Sr. no. | Impurity | Examples | |
|---|---|---|---|
|  |  | Example 8 | Example 9a |
| 1. | Imp-A | 1.303 | ND |
| 2 | Imp-B | 0.008 | 0.012 |
| 3 | Imp-C | 0.025 | 0.018 |
| 4 | Imp-D | 1.887 | 0.011 |
| 5 | Single Max | 0.036 | 0.008 |
|  | Total Imp | 3.296 | 0.049 |

From the above dissolution data that it can be concluded that seal coat enhance the stability of the product.

We claim:

1. A process for preparation of an extended release pharmaceutical composition of Clozapine comprising steps of:
   1) sifting Clozapine with diluents,
   2) preparing granules of clozapine by granulating material of step 1),
   3) extruding the granules of step 2) using an extruder or spheronizing of step 2) using a spheronizer to prepare pellets, beads or spheroids;
   4) seal coating on the extruded granules, pellets, beads or spheroids obtained in step 3);
   5) providing an acidic coating on extruded granules, pellets, beads or spheroids obtained in step 4); and
   6) providing an extended release coating on extruded granules, pellets, beads or spheroids obtained in step 5);
   7) the extended release coated extruded granules, pellets, beads or spheroids are compressed in the form of tablets, mini-tablets or filled in capsules.

* * * * *